United States Patent [19]

Nasu et al.

[11] Patent Number: 5,290,944
[45] Date of Patent: Mar. 1, 1994

[54] METHOD FOR PRODUCING DICHLOROMETHYLPYRIDINES

[75] Inventors: Rikuo Nasu; Taku Shimura; Isamu Katsuyama, all of Yokkaichi, Japan

[73] Assignee: Ishihara Sangyo Kaisha Ltd., Osaka, Japan

[21] Appl. No.: 990,276

[22] Filed: Dec. 14, 1992

[30] Foreign Application Priority Data

Dec. 20, 1991 [JP] Japan .................................. 3-361133
Dec. 26, 1991 [JP] Japan .................................. 3-361411

[51] Int. Cl.⁵ ........................................... C07D 213/26
[52] U.S. Cl. .................................. 546/346; 546/290; 546/314; 546/345
[58] Field of Search ................ 546/346, 345, 290, 314

[56] References Cited

U.S. PATENT DOCUMENTS 4,260,766  4/1981  Morris .
4,499,276  2/1985  Malhotra et al. .
4,499,277  2/1985  Malhotra et al. .

FOREIGN PATENT DOCUMENTS 0030101  6/1981  European Pat. Off. .

OTHER PUBLICATIONS

Tetrahedron Letters, No. 48, 1968, pp. 4951–4952, I. M. Downie, et al., "Reduction of Perhalocompounds with Tertiary Phosphines and Phosphorous Tris (Di-N-Alkyl)Amides".

*Primary Examiner*—C. Warren Ivy
*Assistant Examiner*—D. Margaret M. Mach
*Attorney, Agent, or Firm*—Oblon, Spivak, McClelland, Maier & Neustadt

[57] ABSTRACT

A method for producing a dichloromethylpyridine of the formula (II):

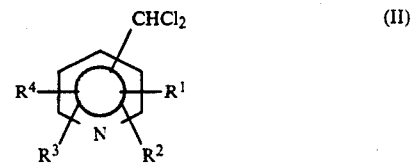

wherein each of $R^1$, $R^2$, $R^3$ and $R^4$ which are independent of one another, is a hydrogen atom, a halogen atom, an alkoxy group or a phenoxy group which may be substituted, provided that $R^1$, $R^2$, $R^3$ and $R^4$ are not simultaneously hydrogen atoms, which comprises reacting a trichloromethylpyridine of the formula (I):

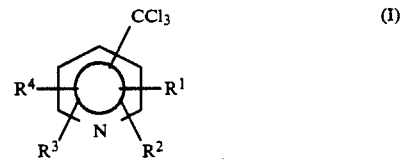

wherein $R^1$, $R^2$, $R^3$ and $R^4$ are as defined above, with a reducing agent, wherein:
(1) a dialkyl phosphite or a trialkyl phosphite is used as the reducing agent, and the reaction is conducted in the presence of a basic substance and an alcohol solvent, or
(2) a trialkyl phosphine or triphenyl phosphine is used as the reducing agent, and the reaction is conducted in the presence of an alcohol solvent.

8 Claims, No Drawings

METHOD FOR PRODUCING DICHLOROMETHYLPYRIDINES

The present invention relates to a method for producing dichloromethylpyridines useful as intermediate materials for e.g. agricultural chemicals or pharmaceuticals.

Several methods have been proposed for the production of dichloromethylpyridines such as 2-chloro-5-dichloromethylpyridine. Among them, there is a method which comprises reducing 2-chloro-5-trichloromethylpyridine which has become readily available on an industrial scale in recent years.

For example, U.S. Pat. No. 4,499,277 discloses a method wherein a trichloromethylpyridine, a reducing agent selected from the group consisting of dialkyl phosphites and trialkyl phosphites and a strong base are treated in the presence of a polar non-hydroxylic solvent and/or a quaternary ammonium phase transfer catalyst to reduce the trichloromethyl group substituted on the pyridine ring to a dichloromethyl group.

On the other hand, in Tetrahedron Letters No. 48, pages 4951–4952, 1968, a method is generally described wherein a trichloromethyl group in a compound having such a trichloromethyl group is converted to a dichloromethyl group in the presence of a tertiary phosphine. However, the only example specifically disclosed there is a method for obtaining benzylidene chloride from benzotrichloride. However, in the method disclosed in the above-mentioned U.S. Pat. No. 4,499,277, a polar non-hydroxylic solvent such as N-methylpyrrolidone is used in a large amount, and there are practical difficulties for industrial operation with respect to the handling and recovery of the solvent.

The present inventors have paid an attention to the conventional method wherein desired dichloromethylpyridines are produced by using as the starting materials trichloromethylpyridines which have become readily available on an industrial scale in recent years and have conducted extensive studies to develop a method whereby the desired products can be produced in large amounts as compared with the conventional method and wherein a solvent which can easily be handled and recovered, is used. It was expected that if a polar hydroxylic solvent such as an alcohol was used in the process of the above-mentioned U.S. Pat. No. 4,499,277, it would undergo a side reaction with the trichloromethyl group of the trichloromethylpyridine or with the halogen atom substituted on the pyridine ring, and the desired reduction reaction would hardly take place. It has been found surprisingly that no substantial side reaction takes place even when an alcohol is used as the solvent, and the desired reduction reaction takes place. The present invention is based on this discovery.

Thus, the present invention provides a method for producing a dichloromethylpyridine of the formula (II):

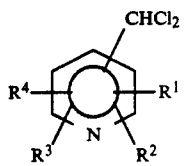

wherein each of $R^1$, $R^2$, $R^3$ and $R^4$ which are independent of one another, is a hydrogen atom, a halogen atom, an alkoxy group or a phenoxy group which may be substituted, provided that $R^1$, $R^2$, $R^3$ and $R^4$ are not simultaneously hydrogen atoms, which comprises reacting a trichloromethylpyridine of the formula (I):

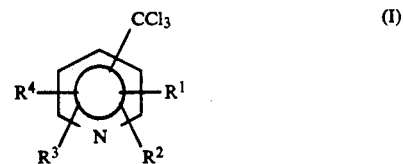

wherein $R^1$, $R^2$, $R^3$ and $R^4$ are as defined above, with a reducing agent, wherein:

(1) a dialkyl phosphite or a trialkyl phosphite is used as the reducing agent, and the reaction is conducted in the presence of a basic substance and an alcohol solvent, or (2) a trialkyl phosphine or triphenyl phosphine is used as the reducing agent, and the reaction is conducted in the presence of an alcohol solvent.

Now, the present invention will be described in detail with reference to the preferred embodiments. In the definition for $R^1$, $R^2$, $R^3$ and $R^4$ in the above formulas (I) and (II), the substituent for the phenoxy group which may be substituted includes a halogen atom, an alkyl group and an alkoxy group. The number of such substituents may be one or more. When the number of substituents is more than one, such a plurality of substituents may be the same or different.

The halogen atom for $R^1$, $R^2$, $R^3$ and $R^4$ may be a fluorine atom, or a chlorine atom, a bromine atom or an iodine atom, and the alkyl group or the alkyl moiety constituting the alkoxy group may be the one having from 1 to 6 carbon atoms, such as methyl, ethyl, propyl or butyl and may be linear or branched.

Typical examples of the trichloromethylpyridine of the formula (I) include 2-chloro-5-trichloromethylpyridine, 2-chloro-3-trichloromethylpyridine, 2,6-dichloro-3-trichloromethylpyridine, 2,3-dichloro-5-trichloromethylpyridine, 2-chloro-6-trichloromethylpyridine, 6-phenoxy-2 -trichloromethylpyridine, 6-phenoxy-5-fluoro-2-trichloromethylpyridine and 6-(4-chlorophenoxy)-2-trichloromethylpyridine. Typical examples of the trichloromethylpyridine of the formula (II) include 2-chloro-5-dichloromethylpyridine, 2-chloro-3-dichloromethylpyridine, 2,6-dichloro-3-dichloromethylpyridine, 2,3-dichloro-5-dichloromethylpyridine, 2-chloro-6-dichloromethylpyridine, 6-phenoxy-2-dichloromethylpyridine, 6-phenoxy-5-fluoro-2-dichloromethylpyridine and 6-(4-chlorophenoxy)-2-dichloromethylpyridine.

However, in the present invention, the trichloromethylpyridine and the dichloromethylpyridine are preferably those of the formulas (I) and (II) wherein each of $R^1$, $R^2$, $R^3$ and $R^4$ is a hydrogen atom or a chlorine atom, provided that they are not simultaneously hydrogen atoms. As the trichloromethylpyridine, 2-chloro-5 trichloromethylpyridine, 2-chloro-3-trichloromethylpyridine, 2,3-dichloro-5-trichloromethylpyridine or 2,6-dichloro-3-trichloromethylpyridine is more preferred. As the dichloromethylpyridine, 2-chloro-5-dichloromethylpyridine, 2-chloro-3-dichloromethylpyridine, 2,3-dichloro-5-dichloromethylpyridine or 2,6-dichloro-3-dichloromethylpyridine is more preferred. Particularly preferred among them, is 2-chloro-5-trichloromethylpyridine for the former and 2-chloro-5-dichloromethylpyridine for the latter.

Now, a case wherein a dialkyl phosphite or a trialkyl phosphite is used as the reducing agent, will be described. The dialkyl phosphite and the trialkyl phosphite may be those wherein the alkyl group constituting them is the one having from 1 to 6 carbon atoms such as methyl, ethyl, propyl, butyl, pentyl or hexyl, preferably the one having from 1 to 4 carbon atoms. For example, the dialkyl phosphite may be dimethyl phosphite, diethyl phosphite, dipropyl phosphite or dibutyl phosphite, and the trialkyl phosphite may be trimethyl phosphite, triethyl phosphite, tripropyl phosphite or tributyl phosphite. A dialkyl phosphite is preferred. Particularly preferred is dimethyl phosphite or diethyl phosphite.

The basic substance may, for example, be an inorganic base, for example, a hydroxide, carbonate or hydrogencarbonate containing a sodium element or a potassium element, such as sodium hydroxide, potassium hydroxide, sodium carbonate, potassium carbonate, sodium hydrogencarbonate or potassium hydrogencarbonate; or a hydroxide or carbonate containing a calcium element or a magnesium element, such as calcium hydroxide, magnesium hydroxide, calcium carbonate or magnesium carbonate, or an organic base, for example, a tertiary alkylamine such as triethylamine; an alkali metal alkoxide such as sodium methoxide; or choline. Preferred is a hydroxide, carbonate or hydrogencarbonate containing a sodium element or a potassium element. Sodium hydroxide or potassium hydroxide is more preferred. Particularly preferred is sodium hydroxide.

The alcohol as the solvent may, for example, be methanol, ethanol, propanol, butanol, pentanol, hexanol or ethylene glycol. A $C_1$-$C_6$ alkanol is preferred. Particularly preferred is methanol or ethanol.

The trichloromethylpyridine, the reducing agent (the dialkyl phosphite or trialkyl phosphite), the basic substance and the solvent may be mixed in a suitable order or may be added stepwise or all at once to conduct the reaction. However, it is usually preferred that the reducing agent is added to a solution having the trichloromethylpyridine dissolved in the solvent, the mixture is cooled so that no side reaction will take place, and then the basic substance is added thereto to conduct the reaction. The amount of the dialkyl phosphite or the trialkyl phosphite as the reducing agent varies depending upon the types of the starting material, the reducing agent, the solvent and the basic substance and the reaction conditions and can not generally be defined. However, it is usually from 1.0 to 50 mols, preferably from 1.0 to 10 mols per mol of the trichloromethylpyridine as the starting material. The amount of the basic substance is usually from 1.0 to 10 mols, preferably from 1.0 to 5.0 mols per mol of the trichloromethylpyridine as the starting material. Such a basic substance may be added all at once or gradually dropwise in the form of an aqueous solution or a solid flake powder. It is preferred to gradually add it in the form of a solid flake powder. When the basic substance is added in the form of an aqueous solution, it is usually advisable to employ a highly concentrated aqueous solution to avoid the above-mentioned side reaction.

The amount of the alcohol used as the solvent is usually from 1 to 40 parts by weight, preferably from 1 to 20 parts by weight, per mol of the trichloromethylpyridine used as the starting material.

The reaction temperature can not generally be defined, but is usually from −20° to +160° C., preferably from −20° to +60° C., and the reaction time is usually from instantaneous to 24 hours, preferably from instantaneous to 6 hours.

The reaction product usually contains the desired dichloromethylpyridine, the alcohol used as the solvent, an organic phosphorus compound produced by the reaction of the alcohol with the reducing agent, salts, etc. By applying usual purification and separation treatments to the reaction product, the desired product can readily be separated, and the solvent can also be readily separated and recovered. For example, if necessary, the reaction product is distilled to recover the alcohol and then poured into water, whereby the desired product can readily be separated.

On the other hand, when the trialkyl phosphine or the triphenyl phosphine is used as the reducing agent, the operation will be as follows.

The reducing agent may be a trialkyl phosphine or triphenyl phosphine. The trialkyl phosphine is preferably the one wherein the alkyl groups constituting it have from 1 to 8 carbon atoms, preferably from 1 to 4 carbon atoms, such as tributyl phosphine or trioctyl phosphine.

The alcohol used as the solvent may be the same alcohol as used for the reduction by the dialkyl phosphite or the trialkyl phosphite.

The amount of the trialkyl phosphine or the triphenyl phosphine used as the reducing agent varies depending upon the types of the starting material, the reducing agent and the solvent and the reaction conditions and can not generally be defined. However, it is usually within a range of from 1.0 to 10 mols, preferably from 1 to 2 mols, per mol of the trichloromethylpyridine used as the starting material. Likewise, the amount of the alcohol used as the solvent is usually from 1 to 40 parts by weight, preferably from 1 to 20 parts by weight. Further, an ether such as tetrahydrofuran may be present in a small amount to improve the solubility of the reactants.

The reaction temperature can not generally be defined, but is usually within a range of from 20° to 160° C., preferably from 50° to 100° C. The reaction time is usually from instantaneous to 100 hours, preferably from instantaneous to 24 hours.

The reaction product thereby obtained may be treated in the same manner as in the case of the reaction product obtained by the reduction by means of the dialkyl phosphite or the trialkyl phosphite. Namely, the desired dichloromethylpyridine can be readily separated from the reaction product by conventional purification or separation operation such as distillation or filtration, and the alcohol used as the solvent can also be readily separated.

Now, the present invention will be described in further detail with reference to Examples. However, it should be understood that the present invention is by no means restricted by such specific Examples.

EXAMPLE 1

2.3 g (0.01 mol) of 2-chloro-5-trichloromethylpyridine was dissolved in 20 ml of ethanol. To this solution, 3.0 g of a 50% sodium hydroxide aqueous solution (0.037 mol of sodium hydroxide) and 1.9 g (0.017 mol) of dimethyl phosphite were added. Stirring was initiated at room temperature (about 20° C.). One or two minutes later, the temperature was raised to about 50° C., and from 20 to 30 minutes later, the mixture was cooled to a temperature of from 20° to 25° C. and reacted at that temperature.

Upon expiration of one hour after the addition of the 50% sodium hydroxide aqueous solution and dimethyl phosphite, the reaction product was analyzed by gas chromatography and found to comprise 58.8% of 2-chloro-5-dichloromethylpyridine, 3.5% of 2-chloro-5-trichloromethylpyridine and 37.7% of others (the others were substances derived from the reducing agent). After completion of the reaction, the reaction mixture was poured into 100 ml of water, and the resulting crystals were collected by filtration. The weight of the crystals was 1.2 g (yield: 60%), and the crystals were analyzed by gas chromatography and found to comprise 95.0% of 2-trichloromethylpyridine and 1.7% of others.

EXAMPLE 2

2.3 g (0.01 mol) of 2-chloro-5-trichloromethylpyridine was dissolved in 20 ml of ethanol. To this solution, 1.9 g (0.017 mol) of dimethyl phosphite was added. The mixture was cooled to about 10° C., and stirring was initiated. Then, 3.0 g of a 50% sodium hydroxide aqueous solution (0.037 mol of sodium hydroxide) was dropwise added thereto over a period of about 30 minutes at a temperature of from 10° to 15° C., and the reaction was continued at the same temperature. Upon expiration of one hour from completion of the dropwise addition, the reaction product was analyzed by gas chromatography and found to comprise 77.7% of 2-chloro-5-dichloromethylpyridine, 1.0% of 2-chloro-5-trichloromethylpyridine and 21.3% of others (others were substances derived from the reducing agent). After completion of the reaction, the reaction mixture was poured into 100 ml of water, and the resulting crystals were collected by filtration.

The weight of the crystals was 1.4 g (yield: 70%), and the crystals were analyzed by gas chromatography and found to comprise 98.6% of 2-chloro-5-dichloromethylpyridine, 1.0% of 2-chloro-5-trichloromethylpyridine and 0.4% of others.

EXAMPLE 3

11.6 g (0.05 mol) of 2-chloro-5-trichloromethylpyridine was dissolved in 100 ml of ethanol. To this solution, 9.4 g (0.085 mol) of dimethyl phosphite was added. The mixture was cooled to about 10° C., and stirring was initiated. Then, 6.0 g of a 50% sodium hydroxide aqueous solution (0.075 mol of sodium hydroxide) was dropwise added thereto over a period of about one hour at a temperature of from 10° to 15° C., and the reaction was continued at the same temperature. Upon expiration of 10 minutes from completion of the dropwise addition, the reaction product was analyzed by gas chromatography and found to comprise 97.2% of 2-chloro-5-dichloromethylpyridine, 2.6% of 2-chloro-5-trichloromethylpyridine and 0.2% of others (in this case, substances derived from the reducing agent were not measured). After completion of the reaction, the reaction mixture was poured into 500 ml of water, and the resulting crystals were collected by filtration.

The weight of the crystals was 8.5 g (yield: 87%), and the crystals were analyzed by gas chromatography and found to comprise 98.6% of 2-chloro-5-dichloromethylpyridine, 1.0% of 2-chloro-5-trichloromethylpyridine and 0.4% of others.

EXAMPLE 4

2.3 g (0.01 mol) of 2-chloro-5-trichloromethylpyridine was dissolved in 20 ml of methanol. To this solution, 1.9 g (0.017 mol) of dimethyl phosphite was added. The mixture was cooled to about 10° C., and stirring was initiated. Then, 3.0 g of a 50% sodium hydroxide aqueous solution (0.037 mol of sodium hydroxide) was dropwise added thereto over a period of about 30 minutes at a temperature of from 10° to 15° C., and the reaction was continued at the same temperature. Upon expiration of 1.5 hours from completion of the dropwise addition, the reaction product was analyzed by gas chromatography and found to comprise 70.4% of 2-chloro-5-dichloromethylpyridine, and 29.6% of 2-chloro-5-trichloromethylpyridine.

COMPARATIVE EXAMPLE 11.0 g (0.10 mol) of dimethyl phosphite was added to 2.3 g (0.01 mol) of 2-chloro-5-trichloromethylpyridine and dissolved. The solution was cooled to about 10° C., and stirring was initiated. Then, 3.0 g of a 50% sodium hydroxide aqueous solution (0.037 mol of sodium hydroxide) was dropwise added thereto over a period of about 30 minutes at a temperature of from 10° to 15° C., and the reaction was continued at the same temperature. Upon expiration of one hour from completion of the dropwise addition, the reaction product was analyzed by gas chromatography and found to comprise 41.1% of 2-chloro-5-dichloromethylpyridine, 58.0% of 2-chloro-5-trichloromethylpyridine and 0.9% of others.

EXAMPLES 5 to 9

11.6 g (0.05 mol) of 2-chloro-5-trichloromethylpyridine was dissolved in 100 ml of an alcohol. To this solution, 9.4 g of dimethyl phosphite or 11.7 g (0.085 mol) of diethyl phosphite was added, and the mixture was cooled to about 0° C. or about 10° C., and stirring was initiated. Then, 6.0 g of a 50% sodium hydroxide aqueous solution (0.075 mol of sodium hydroxide) was dropwise added or 3.4 g of sodium hydroxide flakes or 8.5 g of a 50% potassium hydroxide aqueous solution (0.075 mol of potassium hydroxide) was added thereto over a period of about one hour at a temperature of from −2° to +3° C. or from 10° to 15° C., and the reaction was continued at the same temperature for one hour. After completion of the reaction, the reaction mixture was poured into 500 ml of water, and the resulting crystals were collected by filtration. The crystals were analyzed by gas chromatography to determine the composition, whereby the results shown in Table 1 were obtained.

TABLE 1

| | | | Reaction conditions | | | | | |
|---|---|---|---|---|---|---|---|---|
| | | | Basic substance | | Reaction product | | | Rough yield of CDC (%) |
| Example No. | Alcohol solvent | Reducing agent | Type | Time and temp. for addition | Composition (%) | | Yield (g) | |
| | | | | | CDC | CTC (%) | | |
| 5 | Ethanol | Dimethyl phosphite | NaOH flakes | 1.0 hr −2 to +3° C. | 99.0 | 0.8 | 0.2 | 9.2 | 94% |

TABLE 1-continued

| | Reaction conditions | | | | Reaction product | | | Rough yield of CDC (%) |
|---|---|---|---|---|---|---|---|---|
| | | | Basic substance | | | | | |
| Example No. | Alcohol solvent | Reducing agent | Type | Time and temp. for addition | Composition (%) | | Yield (g) | |
| | | | | | CDC | CTC | (%) | |
| 6 | Ethanol | Diethyl phosphite | 50% NaOH aqueous solution | 1.0 hr 10 to 15° C. | 99.3 | 0.6 | 0.1 | 8.5 | 87% |
| 7 | Ethanol | Dimethyl phosphite | 50% KOH aqueous solution | 0.5 hr 10 to 15° C. | 94.8 | 2.1 | 3.1 | — | — |
| 8 | Methanol | Dimethyl phosphite | NaOH flakes | 1.0 hr 10 to 15° C. | 97.2 | 2.8 | — | 9.3 | 95% |
| 9 | Isopropanol | Dimethyl phosphite | 50% NaOH aqueous solution | 1.0 hr 10 to 15° C. | 88.2 | 16.6 | 0.2 | — | — |

(1) In the column for the composition of the reaction product, CDC and CTC have the following meanings.
CDC: 2-chloro-5-dichloromethylpyridine
CTC: 2-chloro-5-trichloromethylpyridine
(2) In Example No. 7, the reaction and the post treatment were conducted in a 1/5 scale.
(3) In Example No. 7 and No. 9, instead of the composition of crystals, the composition of the reaction mixture was shown.

EXAMPLE 10

284.0 g (1.07 mol) of 2,6-dichloro-3-trichloromethylpyridine was dissolved in 10,044 ml of ethanol. To this solution, 200.0 g (1.82 mol) of dimethyl phosphite was added. The mixture was cooled to about 10° C., and stirring was initiated. Then, 128.4 g of a 50% sodium hydroxide aqueous solution (1.60 mol of sodium hydroxide) was dropwise added thereto over a period of one hour at a temperature of from 10° to 15° C., and the reaction was continued at the same temperature for one hour. After completion of the reaction, ethanol was distilled off, and the obtained oil was washed with water (1000 ml × 3 times) to obtain an oil.

The weight of this oil was 244.2 g (yield: 99%), and the oil was analyzed by gas chromatography and found to comprise 99.6% of 2,6-dichloro-3-dichloromethylpyridine, 0.0% of 2,6-dichloro-3-trichloromethylpyridine and 0.4% of others.

EXAMPLE 11

8.0 g (0.03 mol) of 2,3-dichloro-5-trichloromethylpyridine was dissolved in 60 ml of ethanol. To this solution, 5.6 g (0.051 mol) of dimethyl phosphite was added. The mixture was cooled to about 10° C., and stirring was initiated. Then, 4.1 g of a 50% sodium hydroxide aqueous solution (0.051 mol of sodium hydroxide) was dropwise added thereto over a period of about one hour at a temperature of from 10° to 15° C., and the reaction was continued at the same temperature for one hour. After completion of the reaction, ethanol was distilled off, and the residue was poured into 100 ml of water. The obtained reaction solution was extracted with 100 ml of diethyl ether. The ether layer was washed with water (100 ml × 3 times), and the ether was distilled of to obtain crystals.

The weight of the crystals was 7.0 g (yield: 100%), and the crystals were analyzed by gas chromatography and found to comprise 98.3% of 2,3-dichloro-5-dichloromethylpyridine, 0.0% of 2,3-dichloro-5-trichloromethylpyridine and 1.7% of others.

EXAMPLE 12

6.9 g (0.03 mol) of 2-chloro-5-trichloromethylpyridine was dissolved in 13.8 g (0.3 mol) of ethanol. To this solution, 15.6 g (0.06 mol) of triphenyl phosphine was added, and the mixture was reacted for from 1 to 2 hours under reflux. The reaction product was analyzed by gas chromatography and found to comprise 94.5% of 2-chloro-5-dichloromethylpyridine, 0.7% of 2-chloro-5-trichloromethylpyridine and 4.8% of others. After completion of the reaction, the reaction product was distilled to obtain 1.9 g of 2-chloro-5-dichloromethylpyridine.

EXAMPLE 13

6.9 g (0.03 mol) of 2-chloro-5-trichloromethylpyridine was dissolved in 15 ml of tetrahydrofuran. To this solution, 2.7 g (0.06 mol) of ethanol and 15.6 g (0.06 mol) of triphenyl phosphine were added, and the mixture was reacted for from 14 to 16 hours under reflux. The reaction product was analyzed by gas chromatography and found to comprise 94.9% of 2-chloro-5-dichloromethylpyridine, 4.0% of 2-chloro-5-trichloromethylpyridine and 1.1% of others.

EXAMPLE 14

6.9 g (0.03 mol) of 2-chloro-5-trichloromethylpyridine was dissolved in 55.3 g (1.20 mol) of ethanol. To this solution, 12.1 g (0.06 mol) of tri-n-butyl phosphine was added, and the mixture was reacted for from 1 to 2 hours under reflux. The reaction product was analyzed by gas chromatography and found to comprise 96.3% of 2-chloro-5-dichloromethylpyridine, 1.3% of 2-chloro-5-trichloromethylpyridine and 2.4% of others.

According to the present invention, dichloromethylpyridines useful as intermediate materials for agricultural chemicals or pharmaceuticals can readily be produced by using trichloromethylpyridines as the starting materials and the reducing agent which are readily available at low costs in large amounts. Besides, the yields of the desired products are high, and the handling and recovery of the solvent are easy, as compared with the conventional methods. Thus, the industrial applicability can be improved. As disclosed in Japanese Unexamined Patent Publications No. 218386/1985 and No. 58972/1991, 2-chloro-5-dichloromethylpyridine can be led to an insecticidal compound. The method of the present invention can be used for the production of this 2-chloro-5-dichloromethylpyridine.

We claim:
1. A method for producing a dichloromethylpyridine of the formula (II):

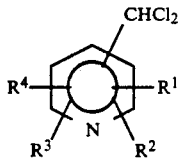

wherein each of $R^1$, $R^2$, $R^3$ and $R^4$ which are independent of one another, is a hydrogen atom, a halogen atom, an alkoxy group or a phenoxy group which may be substituted, provided that $R^1$, $R^2$, $R^3$ and $R^4$ are not simultaneously hydrogen atoms, which comprises reacting a trichloromethylpyridine of the formula (I):

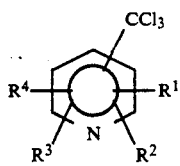

wherein $R^1$, $R^2$, $R^3$ and $R^4$ are as defined above, with a reducing agent, wherein
a dialkyl phosphite or a trialkyl phosphite is used as the reducing agent, and the reaction is conducted in the presence of a basic substance and an alcohol solvent.

2. The method according to claim 1, wherein in each of the formulas (I) and (II), each of $R^1$, $R^2$, $R^3$ and $R^4$ is a hydrogen atom or a chlorine atom, provided that $R^1$, $R^2$, $R^3$ and $R^4$ are not simultaneously hydrogen atoms.

3. The method according to claim 1, wherein the trichloromethylpyridine is 2-chloro-5-trichloromethylpyridine, 2-chloro-3-trichloromethylpyridine, 2,3-dichloro-5-trichloromethylpyridine or 2,6-dichloro-3-trichloromethylpyridine, and the dichloromethylpyridine is 2-chloro-5-dichloromethylpyridine, 2-chloro-3-dichloromethylpyridine, 2,3-dichloro-5-dichlormethylpyridine or 2,6-dichloro-3-dichloromethylpyridine.

4. The method according to claim 1, wherein the reducing agent is a di-$C_1$-$C_4$ alkyl phosphite, the basic substance is a hydroxide, carbonate or hydrogencarbonate of sodium or potassium, and the solvent is a $C_1$-$C_6$ alkanol.

5. The method according to claim 4, wherein the reducing agent is dimethyl phosphite or diethyl phosphite, the basic substance is sodium hydroxide, and the solvent is methanol or ethanol.

6. The method according to claim 4, wherein from 1.0 to 50 mols of the reducing agent, from 1.0 to 10 mols of the basic substance and from 1 to 40 parts by weight of the solvent are used per mol of the trichloromethylpyridine, and the reaction is conducted at a reaction temperature of from $-20°$ to $+160°$ C.

7. The method according to claim 1, wherein 2-chloro-5-dichloromethylpyridine is produced by reacting 2-chloro-5-trichloromethylpyridine with dimethyl phosphite or diethyl phosphite in the presence of a methanol or ethanol solvent and sodium hydroxide.

8. The method according to claim 7, wherein from 1.0 to 10 mols of dimethyl phosphite or diethyl phosphite, from 1.0 to 5 mols of the basic substance and from 1 to 20 parts by weight of the methanol or ethanol solvent are used per mol of 2-chloro-5-trichloromethylpyridine, and the reaction is conducted at a temperature of from $-20°$ to $+60°$ C.

* * * * *